United States Patent [19]
Klein et al.

[11] Patent Number: 5,844,148
[45] Date of Patent: Dec. 1, 1998

[54] DETECTOR WITH ADJUSTABLE SAMPLING TUBES

[75] Inventors: Jeffrey M. Klein, Chicago; Martin L. Krause, Tower Lakes, both of Ill.

[73] Assignee: Pittway Corporation, Chicago, Ill.

[21] Appl. No.: 902,992

[22] Filed: Jul. 30, 1997

[51] Int. Cl.⁶ .................................................. G01N 1/20
[52] U.S. Cl. ..................... 73/563.82; 73/864.81
[58] Field of Search ............................. 73/866.5, 863.43, 73/863.45, 863.41, 863.51–863.55, 863.58, 863.61, 863.81, 863.82, 863.85, 864.33, 864.73, 864.81; 138/120, 109, 155

[56] References Cited

U.S. PATENT DOCUMENTS

| | | | |
|---|---|---|---|
| 2,475,857 | 7/1949 | Reinert | 73/863.51 |
| 3,538,748 | 11/1970 | Linsell et al. | 73/863.61 |
| 3,595,087 | 7/1971 | Starks | 73/863.54 |
| 3,803,921 | 4/1974 | Dieterich | 73/863.51 |
| 5,625,156 | 4/1997 | Serrels et al. | 73/863.51 |

OTHER PUBLICATIONS

HVAC Installer's Notes, System Sensor™, a Division of Pittway.

Installation and Maintenance Instructions, DH400ACDC Air Duct Smoke Detector, System®, a Division of Pittway.

*Primary Examiner*—Robert Raevis
*Attorney, Agent, or Firm*—Rockey, Milnamow & Katz, Ltd.

[57] ABSTRACT

An adjustable sampling tube construction for a duct-mounted smoke detector includes telescopic tube sections which can be fixed in overall length by a screw extending through an outer tube to fix an inner tube with respect to the outer tube. The inner tube includes air sampling holes spaced apart along its length and the outer tube includes a plurality of spaced apart through holes having a same spacing to register with the sampling holes of the inner tube. The inner tube is telescopically positionable within the outer tube to register the sampling holes with the through holes to provide air sampling locations throughout a length of the combined inner and outer tube assembly.

29 Claims, 7 Drawing Sheets

DETECTOR WITH ADJUSTABLE SAMPLING TUBES

FIELD OF THE INVENTION

The present invention relates to detectors for sampling air moving through ducts. More particularly it pertains to sampling tubes which extend into the duct from an externally mounted smoke detector and which sampling air across an air stream profile within the duct.

BACKGROUND

For sampling air within heating, ventilating and air conditioning ducts to detect the presence of smoke, a detector can be mounted externally of the duct. Sampling tubes extend through the duct's wall, into the air flowing in the duct.

The sampling tubes include an open bottom end, typically having an oblique open face. The sampling tubes also include a plurality of sampling ports spaced apart along a length of the sampling tube to effectively sampling the duct air across an air profile. The sampling ports are used to enable the detector to more accurately detect the presence of smoke within the duct.

In a typical installation an inlet sampling tube is provided having its inclined open end facing upstream and its sampling ports spaced along its length also facing upstream. An outlet sampling tube is located downstream of the inlet sampling tube and has its sampling ports and open bottom end facing downstream.

The arrangement of the ports and the open ends ensure a dynamic differential pressure causing air entering the inlet sampling tube to exit the outlet sampling tube, due to air impact pressure within the duct. The air is forced to circulate through the inlet sampling tube into the external detector and out through the outlet sampling tube back into the duct air stream.

The air thus circulated is sampled for the presence of smoke. If smoke is sensed, the detector can be triggered into an alarm mode either to communicate to a remote monitoring station or to trigger a local alarm.

Because HVAC (heating, ventilating and air conditioning) ducts are installed in a variety of sizes depending on the amount of air circulated within the duct, the sampling tubes must be sized to extend an appropriate length into the duct to sampling more accurately across the air stream within the duct. In a known installation procedure, an installer, working at the location of duct, cuts the sampling tubes to length. The length depends on the duct size. The installer then connects the tubes thus cut to the detector for installation in the duct.

It would be advantageous to minimize the field modifications required to install sampling tubes of the correct length into a duct.

SUMMARY OF THE INVENTION

A duct gas sampling system for a detector is provided which increases installation efficiency and effectiveness by reducing installation time and required installation steps. The sampling system includes a detector intended to be mounted externally of the duct with sampling tubes which extend into the duct. The tubes can easily be adjusted in length to adapt to varying duct widths.

In a first embodiment, a sampling assembly includes a first tube fixedly connected to a detector housing and a second tube arranged in telescopic fashion to the first tube for adjustment of the overall length of the first tube and second tube together. A fastener can be used for fixing the adjusted overall length of the first and second tubes. The first and second tubes include spaced apart gas sampling ports along their length, preferably at equal spacing or pitch. Two substantially identical assemblies can be provided for ingress and egress of a fluid such as air or other gases.

In the first embodiment, the fastener includes a screw which is inserted into an unused air sampling port of the first tube and threadingly engages an unused sampling port of the second tube. The combination of first tube and second tube so adjusted include sampling ports along their length which may include sampling ports through a second portion of the second tube which extends outside the first tube, and sampling ports through the first tube which are in registry with sampling ports through the second tube. The first and second tubes can be adjusted in overall length, and fixed in length by inserting the screw through any registering sampling ports of the first and second tube.

In a second embodiment, the sampling assemblies each include a single tubular structure extending from the detector housing and include a collapsible region, such as a corrugated region, which can be elongated or compressed to adjust the overall length of each tube.

In a third embodiment, the sampling assemblies each include a first tube which extends from the detector housing and has a female threaded region on an inside surface thereof. A second tube having a male threaded region on an external surface thereof threadably engages the female threaded region of the first tube. A plurality of air sampling ports is provided through the first and second tubes. Some of the sampling ports of the second tube will be in registry with sampling ports of the first tube as the second tube is adjusted axially, in telescopic fashion, into the first tube by turning the second tube and screwing the second tube into the first tube.

In a fourth embodiment, each sampling tube assembly includes a first tube which extend from the detector housing. The first tube has a plurality of sampling ports.

Also included is a second tube telescopically nested into the first tube. The second tube has a plurality of sampling ports along its length. Some of the sampling ports will be in registry with the sampling ports of the first tube when the second tube is inserted into the first tube.

The second tube also includes snap-locking elements such as a resilient tab, a spring-loaded button, a slotted bayonet connection or a snap ring. These elements can be used to selectively adjust the relative position of the second tube inside the first tube to adjust the overall length of the first tube and the second tube together.

In a fifth embodiment, the overall length of a sampling tube assembly is adjusted by attaching incremental tube sections to build up an overall length of the sampling tube assembly corresponding to the size of the duct. The sections of tube can be standardized components for cost effectiveness. The tube sections can be interconnected end to end using a male and a female coacting socket formation at opposite ends of each section. A snap engagement can be effected by tabs, annular snap rings, spring-loaded buttons, or screws to build up an overall length of the sampling tube assembly. Each section can have one or more sampling ports along its length.

According to the various embodiments of the invention, during field installation, an installer need not perform a cutting operation to size a sampling tube, and in some cases need not undertake a precise measuring step. Sampling assemblies which embody the present invention enable an installer to effectively and accurately adjust sampling tube assemblies for a plurality of sizes of ducts.

The components of the sampling tube assemblies of the present invention provide for a spaced-apart location of sampling ports to provide an accurate assessment of the presence of smoke or other constituents within a duct. The present sampling tube assemblies are particularly advantageous for ducts eighteen inches or less in width, although the invention is not limited to that size range.

Other features and advantages of the present invention will become readily apparent from the following detailed description of the accompanying drawings, and the appended claims.

DETAILED DESCRIPTION OF THE PREFERRED EMBODIMENTS

Figure 1:
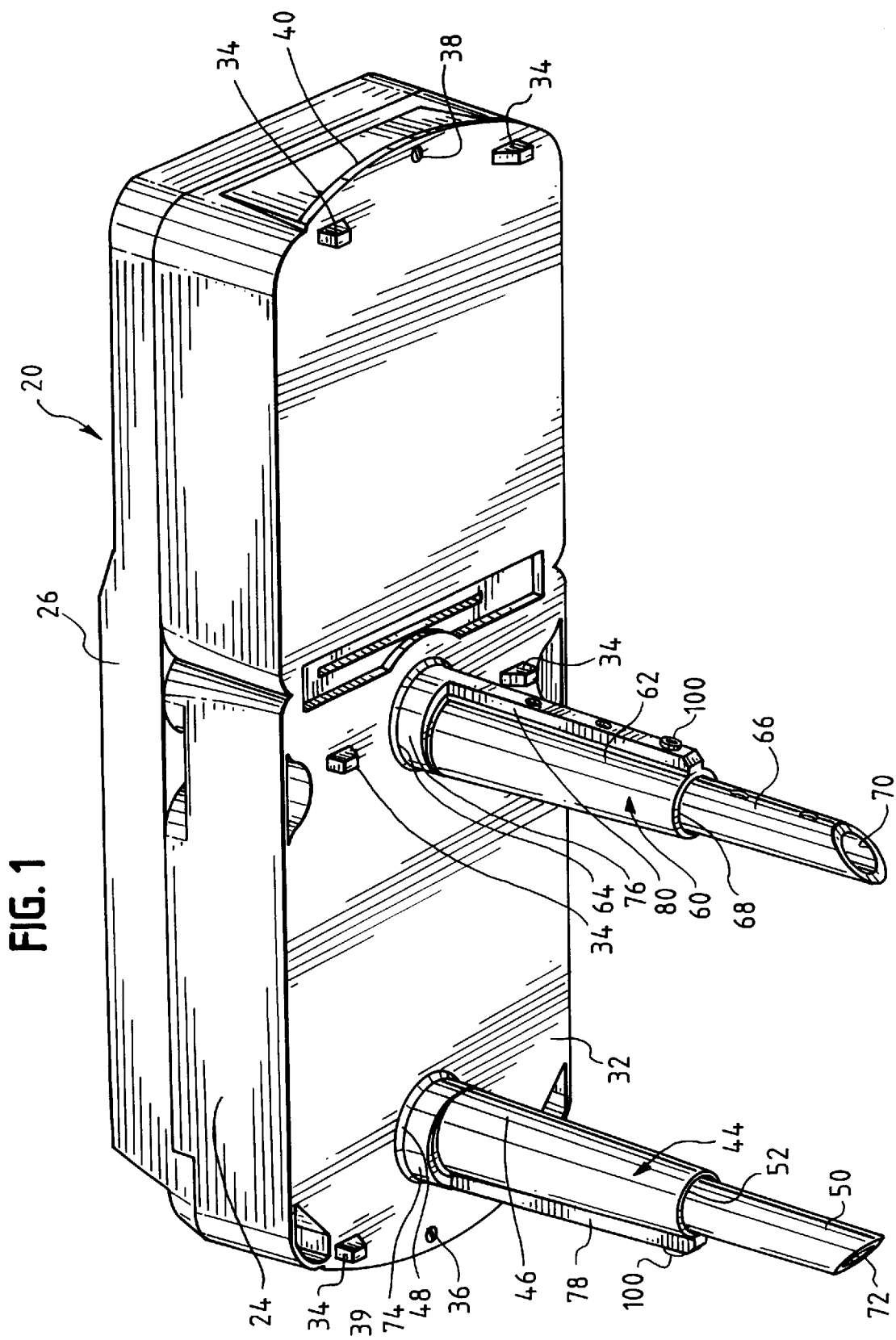
FIG. 1 is a perspective view of a first embodiment detector of the present invention.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

Figure 2:
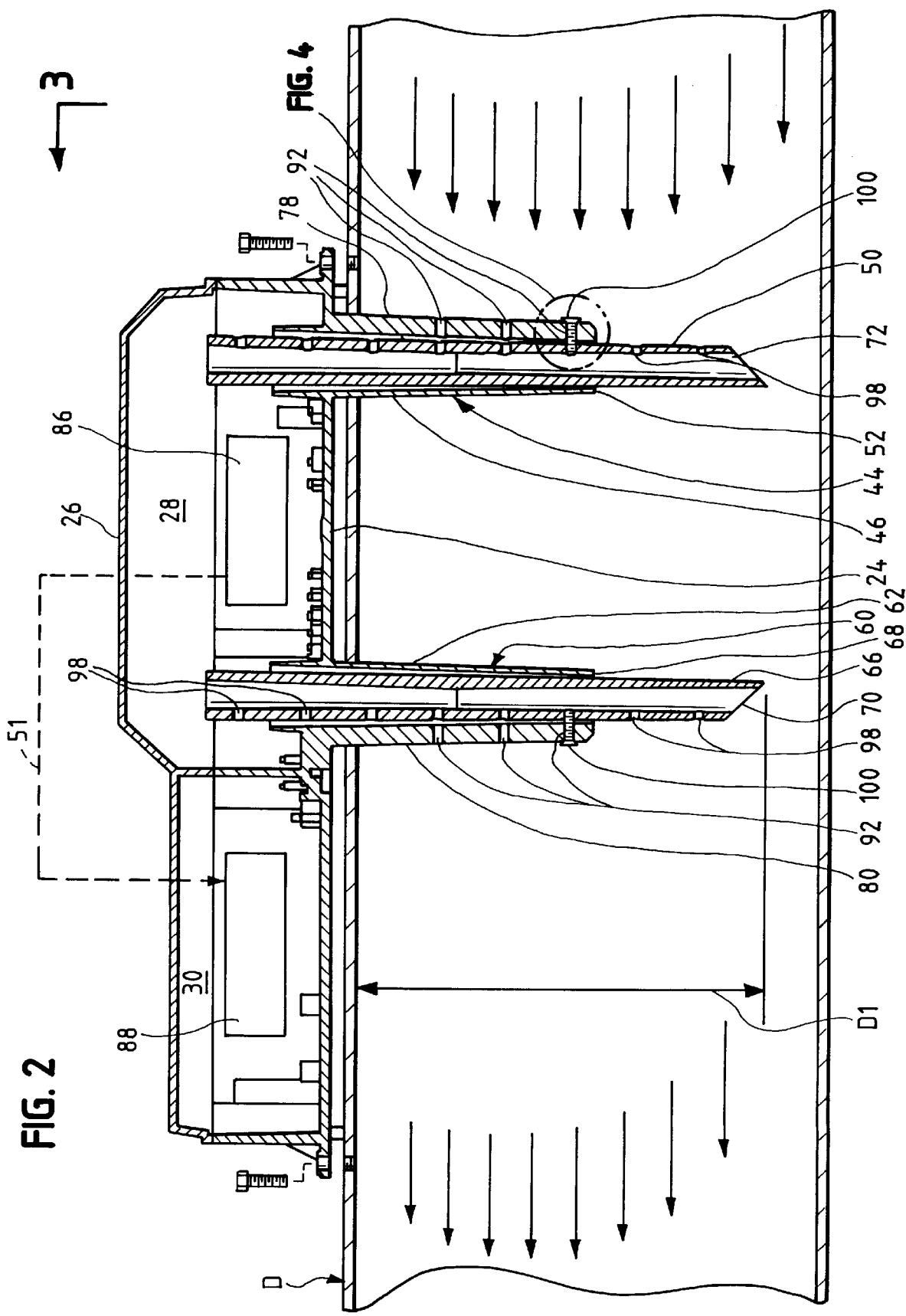
FIG. 2 is a cross-sectional, partially schematic, view of the detector of FIG. 1.
Figure 3:
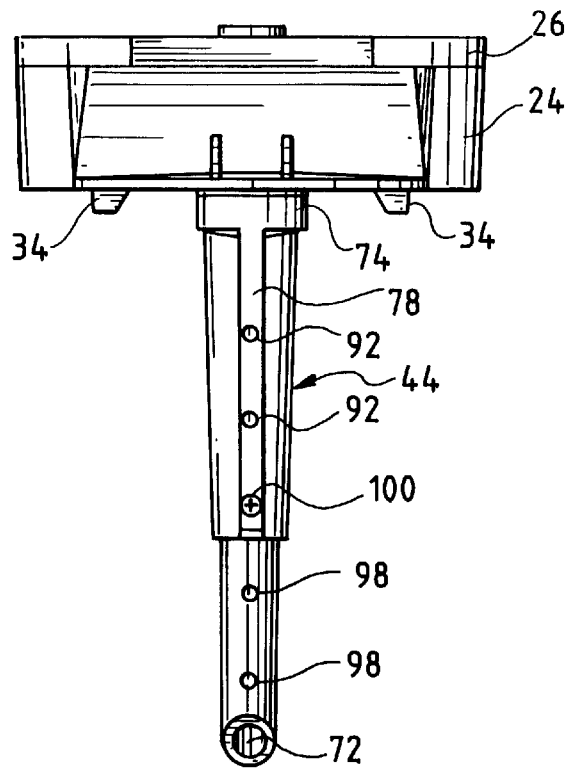
FIG. 3 is a side view taken generally along the plane 3—3 of FIG. 2.

FIGS. 1 through 4 illustrate a detector 20 which includes a housing 24 closed by an overlying cover 26. A sensing cavity 28 and an electronics cavity 30 are formed between the cover 26 in the housing 24 (as shown in FIG. 2). A bottom surface 32 of the housing 24 provides a plurality of feet 34 for supporting the housing 24 on a duct D. Screw receiving holes 36, 38 are provided through overhanging ledges 39, 40 of the bottom surface 32 for attaching the housing 24 to the duct D.

Extending from the bottom surface 32 are inlet and outlet sampling tube assemblies 44, 60 which are open into the sensing cavity 28. The inlet sampling tube assembly 44 includes a first inlet tube 46 connected at a base end 48 to the housing 24 and a second inlet tube 50 having a portion telescopically received into a distal end 52 of the first inlet tube 46.

Spaced from the inlet sampling tube assembly 44 is the outlet sampling tube assembly 60 having a first outlet tube 62 fixedly connected at a base end 64 to the housing 24. A second outlet tube has a portion 66 telescopically fit into a distal open end 68 of the first outlet tube 62.

The second outlet tube 66 includes an oblique open end 70 which is inclined toward a downstream side of the duct while the second inlet tube 50 includes an oblique open end 72 inclined toward the inlet upstream side of the duct. The oblique open ends serve as sampling ports for receiving air through the oblique open end 72 and returning air through the oblique end 70.

The first inlet tube 46 is reinforced at its base end 48 with a first collar 74. The first outlet tube 62 is reinforced at its base end 64 with a second collar 76. The collars 74, 76 extend around the circumference of the respective tubes 46, 62. Extending axially from the collar 74, 76 are ribs or bosses 78, 80 respectively.

Referring now to FIG. 2, within the sensing cavity 28 is located an air constituent detector 86, such as a smoke detector. A smoke detector can be implemented, for example, as an ionization type detector which continuously samples an air stream and outputs a signal S1 indicative thereof. Other types of sensors can be used without departing from the spirit and scope of the invention. Within the electronics cavity 30 is an electronics module 88 which includes a circuit board and electric wire terminals for receiving the signal S1 and conditioning the signal in known fashion to be received by a remote monitor or for providing a local alarm.

It can be observed from FIG. 2 that the constructions of the inlet sampling tube assembly 44 and the outlet sampling tube assembly 60 are substantially identical but oriented so as to be mirror images of one another.

The ribs 78, 80 include a plurality of through holes 92 spaced apart along a length of the respective tubes 78, 80. Additionally, the second inlet tube 50 and the second outlet tube 66 include a plurality of sampling holes 98 spaced apart along the length of the respective tubes 50, 66. Preferably, the sampling holes 98 are spaced apart at the same spacing or pitch as are the through holes 92 of the first tubes 46, 62. The through holes 92 and sampling holes 98 form air sampling ports either alone or together by being in registry with each other.

The second tubes 50, 66 are each slidably received into the respective first tubes 46, 62. The relative depth D1 of each assembly within the duct D can be adjusted. To adjust this depth, the second tubes 50, 66 are slid within the first tubes 46, 62 to set the over-all length of each assembly. At least one screw 100 is respectively inserted into a through hole 92 and engaged in a sampling hole 98 for each assembly 44, 60.

Figure 4:
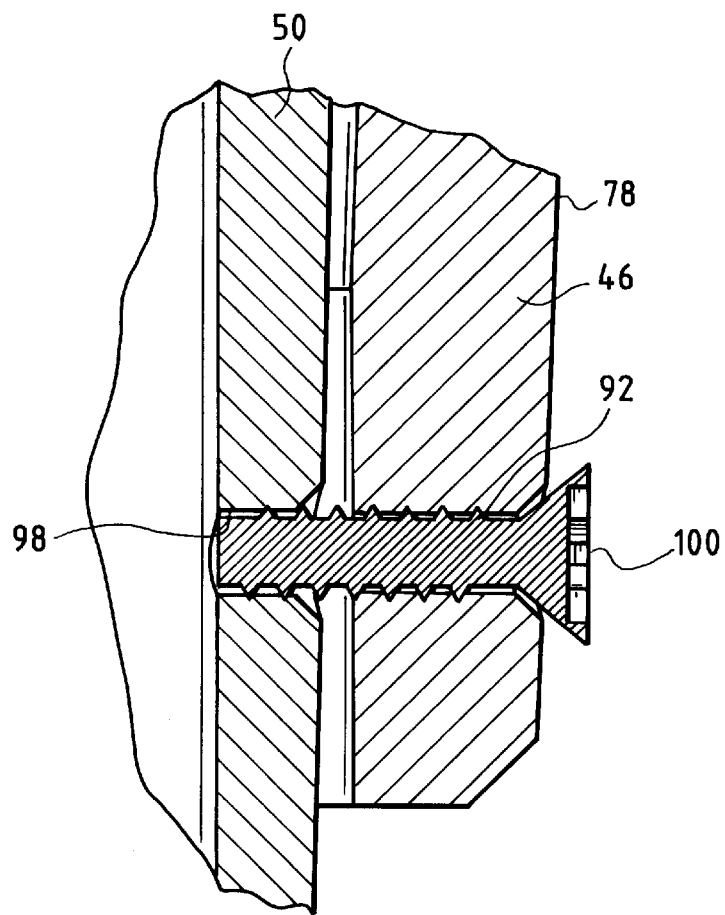
FIG. 4 is an enlarged sectional view taken from FIG. 2.

As demonstrated in FIGS. 1 and 4, the screw and sampling holes are relatively sized such that the screw is self tapping into the wall of the respective second tubes 50, 66. The through holes 92 can also be sized such that the screw 100 is self tapping through the respective wall of the first tubes 46, 62, however, this is not a requirement.

When the two screws 100 are engaged, the sampling tube assemblies 44, 60 can include some sampling holes 98 extending below the open end 52, 68 of the respective first tubes 46, 62 and other sampling holes 98 which are within the first tubes 46, 60 but which are in registry with the through holes 92 such that air can pass from outside the sampling tubes 44, 60 to inside the second tubes 46, 62.

Air is sampled by the inlet sampling tube assembly 44 through the through holes 92 and/or the sampling holes 98 and through the oblique open end 72. Air is passed into the sensor cavity 28, sensed for constituents such as smoke, and returned to the duct via the outlet sampling tube assembly 60. Particularly, air is returned via the through holes 92 and/or the sampling holes 98 and the oblique open end 70 of the outlet sampling tube assembly 60.

It should be noted that further holes can be provided along the length of one or both tubes 46, 50; 62, 66 and can be dedicated to fixing the axial length of the assemblies 44, 60 separate and distinct from the holes 92, 98, which can be dedicated to air sampling. Although the use of a spare air sampling port made of registering holes 92, 98 for receiving a fixing screw is an advantage of the invention, such dual purpose of the holes 92, 98, is not required. The use of separate and distinct axial length fixing holes and air sampling holes is also encompassed by the invention.

Figure 5:
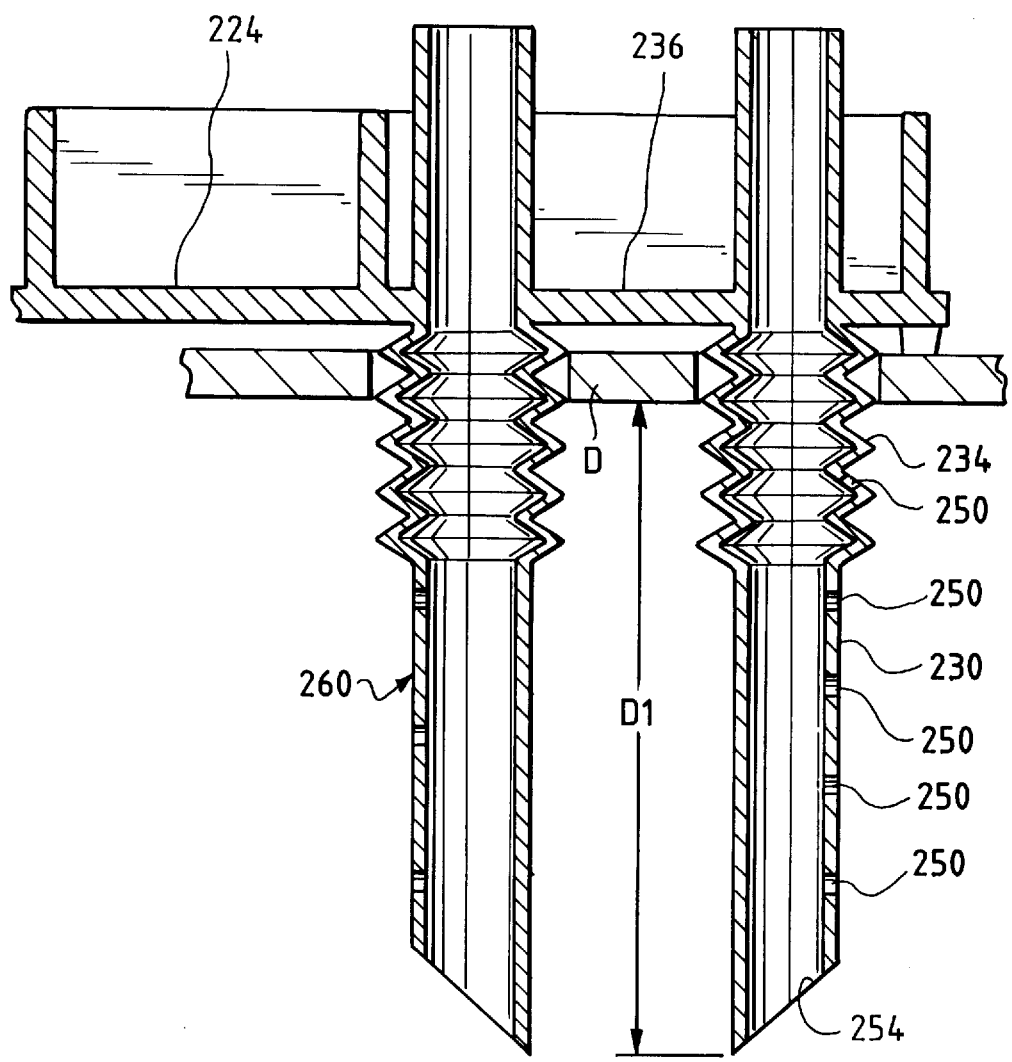
FIG. 5 is a schematic sectional view of a second embodiment of the present invention.

FIG. 5 illustrates a second embodiment. A housing 224 includes, extending therefrom, an alternate inlet tube assembly 230 having an accordion or corrugated region 234 adjacent a bottom wall 236 of the housing 224.

The tube assembly 230 can be molded with, adhesively secured to, threaded into, or otherwise connected to the bottom wall 236. The tube 230 includes a plurality of sampling ports 250 spaced along a length thereof facing in an upstream direction. The tube 230 includes an inclined open end 254, also facing in an upstream direction.

To adjust the overall depth D1 of the tube assembly 230 inside of the duct D, the tube assembly 230 can be forcibly stretched or compressed within the corrugated region 234 to set the length of the tube. The accordion region 234 is sufficiently stiff to retain the length setting. The accordion region 234 can also be provided with sampling ports 250 as required.

An outlet tube assembly 260 can be provided which is a mirror image construction and orientation to that of the inlet tube assembly 230. The assembly 260 can, but need not be, set to the same length as the assembly 230.

Figure 6:
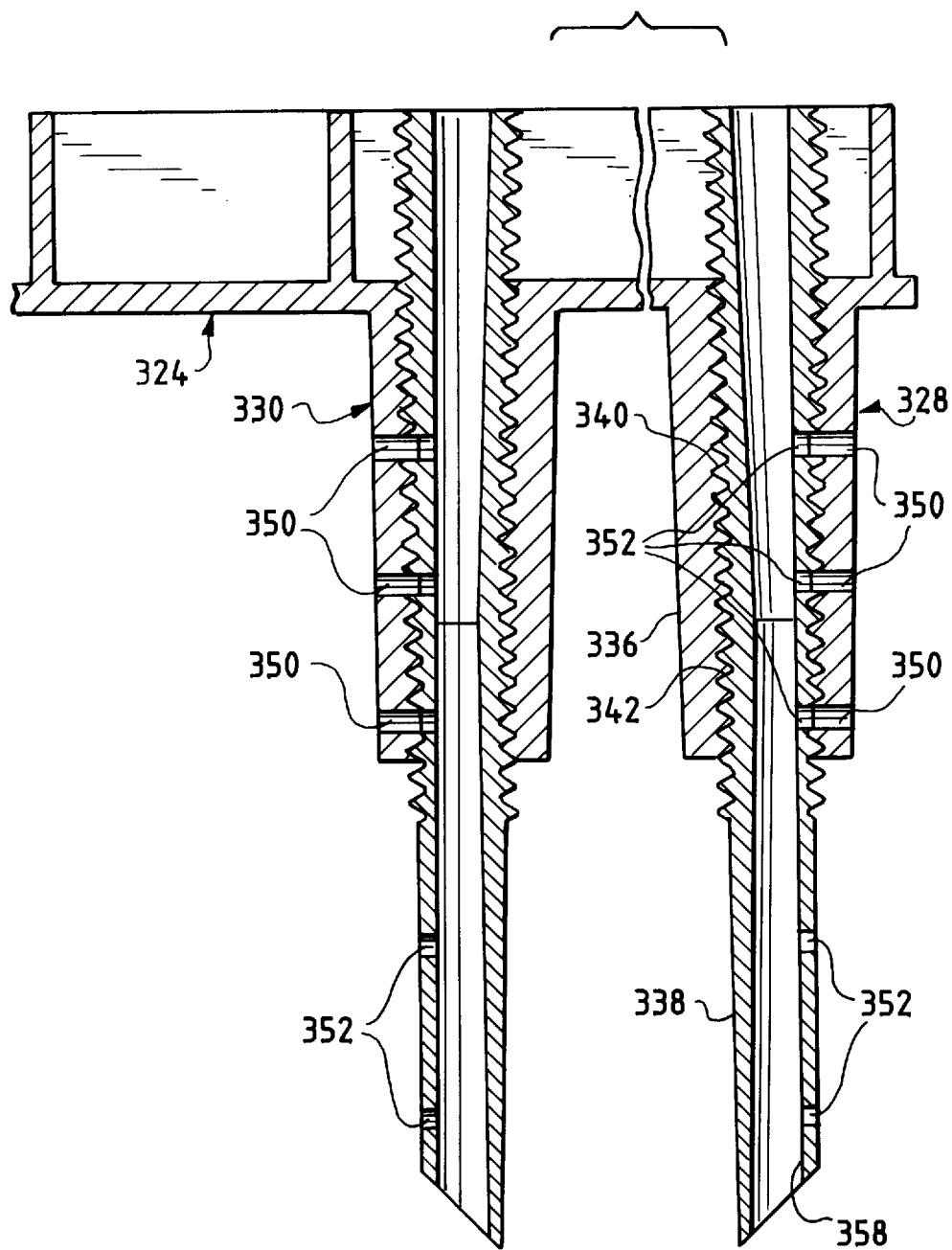
FIG. 6 is a schematic sectional view of a third embodiment of the present invention.

FIG. 6 illustrates a third embodiment. An alternate housing 324 is provided having extending therefrom an inlet tube assembly 328 and an outlet tube assembly 330. As with the previous embodiments, the inlet tube and outlet tube assemblies can be identically constructed and oriented in mirror image fashion relative to one another.

The inlet tube assembly 328 includes a first inlet tube 336, and a second inlet tube 338 telescopically received within the first inlet tube 336. The first inlet tube 336 has a female threaded surface 340 on an inside surface thereof. Threads 340 rotatably engage a male threaded outside surface 342 of the second inlet tube 338. The tube assembly 328 can be adjusted in overall length by rotating the second tube 338 into the first tube 336 to establish a desired length.

The first tube 336 includes a plurality of spaced apart through holes 350. The second tube 338 includes a plurality of spaced apart sampling holes 352 which preferably are spaced apart at the same spacing as the through holes 350 such that a plurality of the sampling holes 352 can be set in registry with the through holes 350.

The second inlet tube 338 also includes an open inclined bottom end 358 facing in an upstream direction as are the holes 350, 352. A thread fixing compound or a self tapping screw or other means (not shown) can be used to fix the two tubes 336, 338 to prevent rotation therebetween after adjustment.

Assembly 330 has the same structure and characteristics as does the assembly 328.

Figure 7:
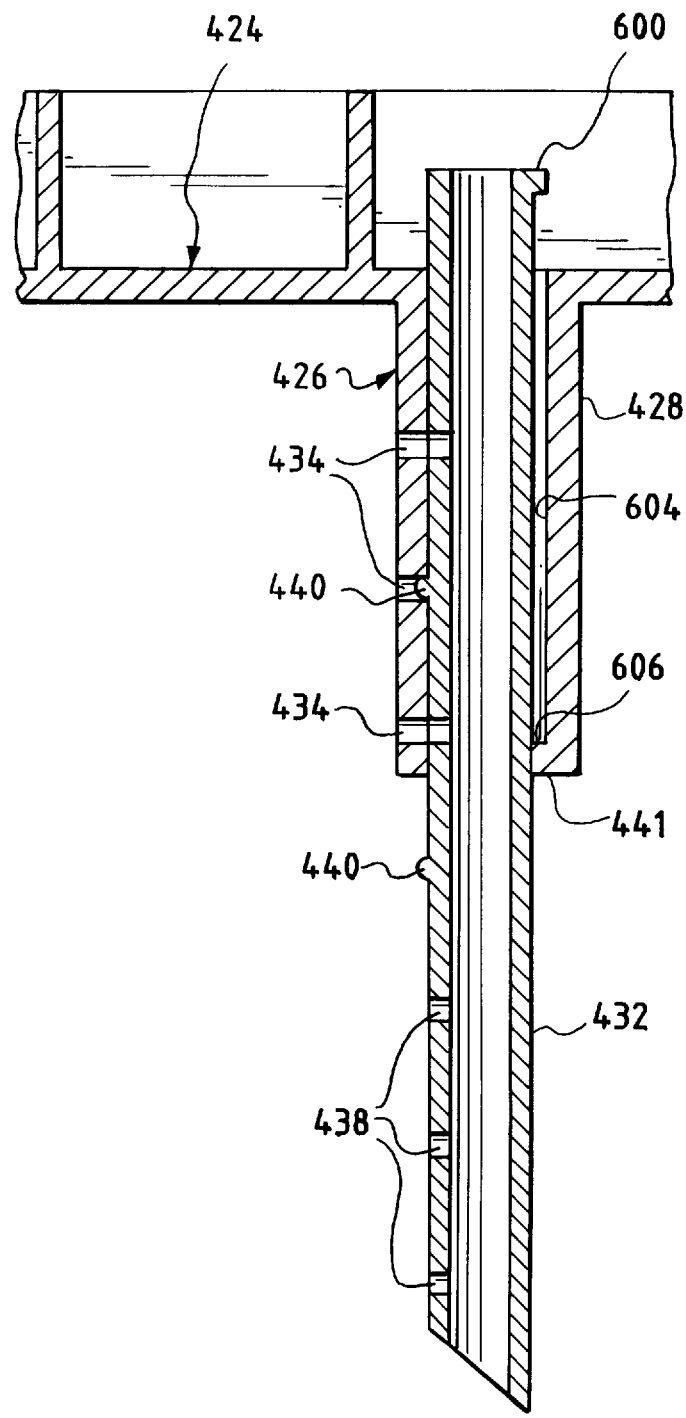
FIG. 7 is a schematic partial sectional view of a fourth embodiment of the present invention.

FIG. 7 discloses a portion of a fourth embodiment. A housing 424 includes an outlet tube assembly 426 and an inlet tube assembly (not shown) spaced from the outlet tube assembly. As with the other embodiments, the inlet tube assembly can be an identical construction with the outlet tube assembly and oriented in mirror image fashion.

The outlet tube assembly 426 includes a first outlet tube 428 extending from the housing 424 and a second outlet tube 432 received in telescopic fashion within the first outlet tube 428. The first outlet tube 428 includes a plurality of through holes 434 facing in the downstream direction. The second outlet tube 432 includes a plurality of sampling holes 438 spaced apart along a length of the second outlet tube 432. Preferably, the sampling holes 438 are spaced apart to register with the through holes 434 at plural positions of length adjustment of the second outlet tube 432 with respect to the first outlet tube 428.

An element for selectively and adjustably connecting the second outlet tube 432 to the first outlet tube 428 is provided in the form of protuberances, buttons, tabs or detents 440 which can be received into selected through holes 434 or alternatively into dedicated holes located elsewhere around the circumference of the first tube 428 (not shown). The through holes 434 need not serve a dual function of being air sampling ports and also being fixing holes for attaching the second tube 432 to the first tube 428, although that is one advantage of the invention.

It should be noted that the detents 440 can be flexible members for force fitting into the first tube 428 through an open end 441 thereof. The detents 440 rebound into the through holes 434 to fix the relative axial and rotary position of the tubes. Alternatively, the detents can be replaced by spring-loaded buttons which retract for forcing the tube 432 into the open end 441 of tube 428 and rebound under spring urging into the through holes 434.

It should also be noted that the relative location of the tabs 440 and the through holes 434 can be reversed such that the tabs or other attaching protuberance can extend from the first tube 428 toward the second tube 432 and can be received into the sampling holes 438. It is also within the scope of the invention that the detents, tabs or protuberances can be rounded cylinders or annular rings or other shapes which mutually engage between the first and second tubes 428, 432.

Figure 8:
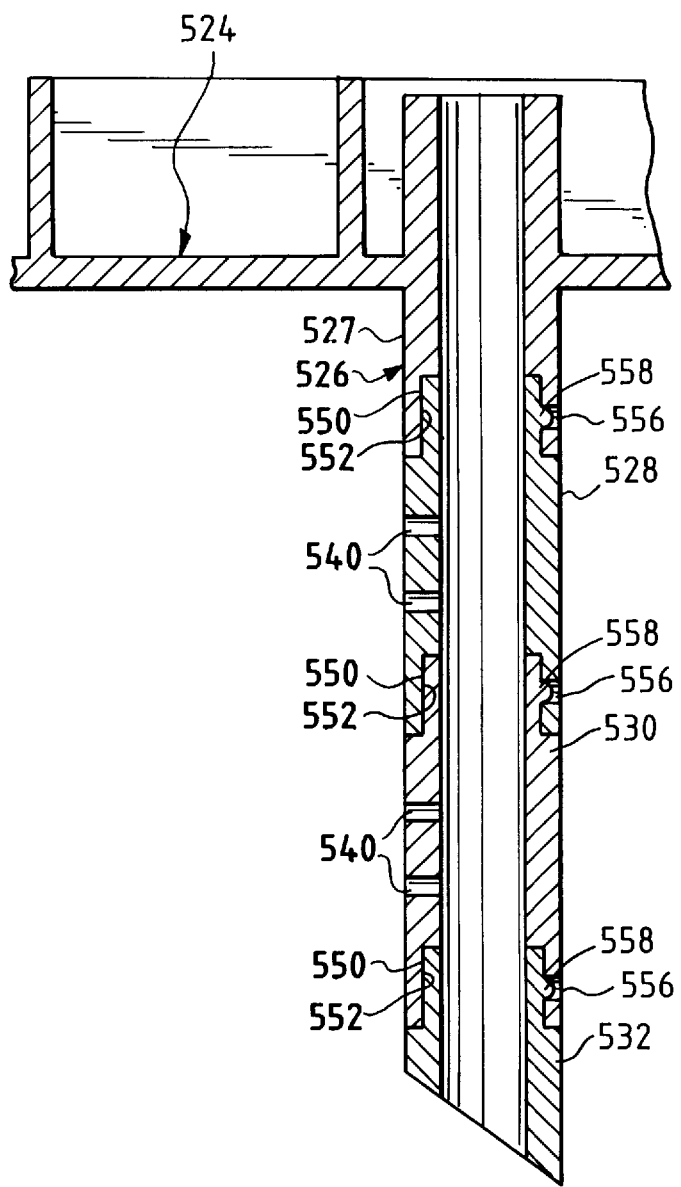
FIG. 8 is a partial sectional schematic view of a fifth embodiment of the present invention.

FIG. 8 illustrates a fifth embodiment. A housing 524 includes an outlet sampling tube assembly 526 and an identically configured inlet tube assembly (not shown) oriented in mirror image fashion. The outlet tube assembly includes a first tube portion 527 extending into and from the housing 524 and fixed thereto.

The tube assembly 526 includes additional tube segments 528, 530, 532 which snap together to build up the desired length of the tube assembly 526. Intermediate segments 528, 530 can be identical and can be provided in quantities of one, two, or more sections to build up the entire length of the tube 526. An end section 532 includes an angled open end 536 facing in the downstream direction. Each section 528, 530, 532 includes one or more through holes 540 facing in the downstream direction.

The sections, 527, 528, 530, 532 are interconnected using an interengaging socket and plug formation formed at each joint between tube sections. The first tube portion 527 includes a socket 550 for receiving a plug end 552 of the next intermediate tube section 528. The socket can include a fixing hole 556 for receiving a tab 558 of the plug end 552 for locking the sections 527, 528 together. The socket and plug end and fixing hole and tab are repeated at each interface between the sections 528–530 and 530–532.

It should be noted that other methods of axially snap-connecting tube sections to build up a desired length are encompassed by the invention. Using set screws to lock telescoping sections such as shown in FIG. 2, or screw threading such as shown in FIG. 6 can also be applied to the embodiment of FIG. 8.

As contemplated by all the described embodiments, both inlet and outlet sampling tube assemblies are configured for easy, on site adjustment and installation, simplifying assembly of duct detectors and reducing the costs associated therewith.

As a further development of the invention, provision can be made to loosely retain together the two adjustably positionable sampling tubes which make up each sampling tube assembly, such as the tube pair 46, 50, shown in FIG. 1, or the tube pair 336, 338 shown in FIG. 6, or the tube pair 428, 432 shown in FIG. 7. That is, the sampling tubes of each pair would be prevented from separating, while maintaining freedom to axially move relative to each other to adjust the overall length of the sampling tube assembly.

As illustrated in FIG. 7, this provision can be accomplished by using an end stop 600 on one of the sampling tubes 432 of the respective sampling tube assembly, which end stop would travel axially in a slot 604 formed in the respective other tube 428 of the sampling tube assembly during length adjustment. The slot 604 would terminate at a closed end 606 which would abut the end stop 600 to prevent further axial movement of the one sampling tube with respect to the other sampling tube, i.e., at the most extended configuration of the sampling tube assembly.

Alternatively, one of the tubes of the sampling tube assembly can include an inwardly directed ledge or shoulder and the other tube of the sampling tube assembly can include an outwardly directed annular lip which would abut the ledge at the most extended position of the sampling tube assembly. Other means of retaining the two tubes together to prevent separation, while allowing axial adjustment, include tethering the two tubes together or tethering the extendible tube of the pair to the detector housing.

By retaining the two pairs together, the sampling tube assemblies can be preinstalled as a complete assembly at the factory, and the field installer need only adjust and fix the length of the tube pairs. Thus, an additional loose part, and an additional step to install the loose part, can be avoided.

From the foregoing, it will be observed that numerous modifications and variations can be effected without departing from the spirit and scope of the novel concept of the present invention. It is to be understood that no limitation with respect to the specific embodiments disclosed herein is intended or should be inferred. The disclosure is intended to cover by the appended claims all such modifications as fall within the scope of the claims.

What is claimed:

1. A sampling tube assembly for a detector having a housing, comprising:

a first tube section having a base end and a first distal end, said first tube section connectable to the detector housing at said base end and extending from the detector housing to said first distal end;

a second tube section extending from said first distal end of said first tube section, and having a second distal end spaced from said first distal end, said second tube section including at least one sampling port;

said first tube section and said second tube section arranged for adjustably varying the distance between said housing and said second distal end of said second tube section; and a plurality of holes spaced apart along a length of one of said first and second tube sections, a first portion of said first tube section and a second portion of said second tube section nested telescopically to adjust the relative overall length of said first tube section and said second tube section, and a radially extending elongate member arranged to engage one of said holes of said plurality of said holes and a fixed position on a respective other of said first tube section and said second tube section.

2. The sampling tube assembly according to claim 1, wherein said plurality of holes is arranged on said second tube section, said second portion of said second tube section is telescopically nested inside said first portion of said first tube section, and said first tube section includes at least one hole therethrough registrable with said plurality of holes at plural telescopic positions of said second tube section with respect to said first tube section; and wherein said elongate member comprises a fastener fit into said one hole of said first tube section and engaged into a select one of said plurality of holes in said second tube section.

3. The sampling tube assembly according to claim 2, wherein said first tube section includes a plurality of spaced apart holes which are spaced apart along a length thereof at a same interval as said plurality of holes are spaced apart along said length of said second tube section and said fastener is interfit into one pair of registering holes of said plurality of holes of said first and second tube sections to fix a relative position of said second tube section within said first tube section, and a plurality of pairs of holes of said first and second tube sections are in registry to function as air sampling ports.

4. The sampling tube assembly according to claim 3, wherein said first tube section includes a reinforcing rib along a length thereof, said plurality of holes through said first tube section passing through said reinforcing rib.

5. The sampling tube assembly according to claim 1 wherein one of said first and second tube sections includes at least one hole therethrough registrable with a plurality of holes arranged through a respective other of said first and second tube sections at plural telescopic positions of said second tube section with respect to said first tube section; and wherein said elongate member comprises a fastener fit into said one hole and engaged into a select one of said plurality of holes.

6. A sampling tube assembly for a detector having a housing, comprising:

a first tube section having a base end and a first distal end, said first tube section connectable to the detector housing at said base end and extending from the detector housing to said first distal end;

a second tube section extending from said first distal end of said first tube section, and having a second distal end spaced from said first distal end, said first tube section and said second tube section each including at least one sampling port; and said first tube section and said second tube section arranged for adjustably varying the distance between said first distal end of said first tube section and said second distal end of said second tube section.

7. The sampling tube assembly according to claim 6, comprising a plurality of tube sections snap-fittingly engagable between said first tube section and said second tube section.

8. The sampling tube assembly according to claim 6, comprising a plurality of incremental tube sections attachable between said first tube section and said second tube section.

9. The sampling tube assembly according to claim 6, comprising female threads on an inside surface of said first tube section, and male threads on an outside surface of said second tube section, said male and female threads sized to threadingly engage and said second tube section screwable into said first tube section to adjust the overall length of said first tube section and second tube section.

10. The sampling tube assembly according to claim 6, comprising a corrugated region arranged between said tube sections which can be stretched or compressed to set said overall length.

11. The sampling tube assembly according to claim 6, comprising at least one separate intermediate tube section connected between said first distal end of said first tube section and said second distal end of said second tube section.

12. The sampling tube assembly according to claim 11, wherein said at least one intermediate tube section comprises a plurality of intermediate tube section each having an identical configuration.

13. The sampling tube assembly according to claim 6 wherein said sampling ports of said first and second tube sections open into a common pathway.

14. The sampling tube assembly according to claim 13 wherein said common pathway comprises an inside volume of said second tube section.

15. The sampling tube assembly according to claim 6 wherein said first and second tube sections are relatively sized to be at least partially nested together telescopically, to adjust the relative overall length of said first tube section and said second tube section, and said assembly comprises a plurality of first holes spaced apart along a length of said first tube section and a plurality of second holes spaced apart along a length of said second tube section, at least one of said first holes alignable with one of said second holes at plural telescopically adjusted positions of said first tube section with respect to said second tube section to form at least one sample port extending through both of said first and second tube sections.

16. The sampling tube assembly according to claim 15 wherein said at least one of said first holes includes two first holes and said at least one of said second holes includes two second holes.

17. The sampling tube assembly according to claim 6 wherein said first and second tube sections are relatively sized to be at least partially nested together telescopically to adjust the relative overall length of said first tube section and said second tube section.

18. The sampling tube assembly according to claim 6, wherein said first tube section includes an abutment and said second tube section includes an end stop, said abutment and said end stop arranged to engage at a maximum value of said distance for preventing axial separation of said first and second tube sections while allowing relative axial movement between said first and second tube sections.

19. A sampling tube assembly for a detector having a housing, comprising:
    a first tube section having a base end and a first distal end, said first tube section connectable to the detector housing at said base end and extending from the detector housing to said first distal end;
    a second tube section extending from said first distal end of said first tube section, and having a second distal end spaced from said first distal end, said second tube section including at least one sampling port;
    said first tube section and said second tube section arranged for adjustably varying the distance between said housing and second distal end of said second tube section;

wherein said second tube section is sized to be at least partially nested into said first tube section, and said assembly comprising a plurality of first holes spaced apart along a length of said first tube section and a plurality of second holes spaced apart along a length of said second tube section with a same pitch as said first holes, said first tube section includes a reinforcing rib extending axially on an outside thereof, said plurality of first holes penetrating through said reinforcing rib; and a radially extending fastening member penetrating one of said first holes and one of said second holes to fix the relative axial position between said first and second tube sections.

20. A duct mountable detector, comprising:
a detector housing including a sensing cavity;
a first tube section connected to said detector housing open into said sensing cavity, said first tube extending to a distal end portion;
a second tube section having a first end portion connected to said first tube section, said second tube section extending from said distal end portion of said first tube section, and having a second end opposite said first end portion, said first tube section and said second tube section each having at least one sampling port; and
wherein said first tube section and said second tube section are connected together and are relatively adjustable for fixing the distance between said housing and said second end of said second tube section, said sampling ports of said first and second tube sections open into a common axially arranged pathway which is open into said sensing cavity.

21. The detector sampling tube according to claim 20, comprising a plurality of holes spaced apart along a length of one of said first and second tube sections, and a fastener arranged to engage one of said holes of said plurality of said holes and a fixed position on a respective other of said first tube section and said second tube section.

22. The detector according to claim 21, further comprising a third tube section connected to said detector housing open into said sensing cavity and spaced from said first tube section, said third tube section extending to a distal end portion thereof;
    a fourth tube section having a first end portion connected to said third tube section, and extending from said distal end portion of said third tube section, and having a second end opposite said third end portion, said third tube section telescopically arranged with said fourth tube section, said fourth tube section having at least one port opening through said fourth tube section;
    said at least one sampling port of said second tube section arranged to be facing upstream in an air flow direction within the duct, said at least one port opening of said fourth tube section arranged to be facing downstream in the air flow direction within the duct.

23. The duct mountable detector according to claim 20, wherein said first tube section includes an abutment and said second tube section includes an end stop, said abutment and said end stop arranged to engage at a maximum value of said distance for preventing axial separation of said first and second tube sections while allowing relative axial movement between said first and second tube sections.

24. The detector according to claim 20 wherein said second end of said second tube section is slidably adjustable in position within said distal end portion of said first tube section.

25. The detector according to claim 20, wherein said common axially arranged pathway is an inside volume of said second tube section.

26. The detector according to claim 20 wherein said first and second tube sections are relatively sized to be at least partially nested together telescopically, to adjust the relative overall length of said first tube section and said second tube section, and said assembly comprises a plurality of first holes spaced apart along a length of said first tube section and a plurality of second holes spaced apart along a length of said second tube section, at least one of said first holes alignable with one of said second holes at plural telescopically adjusted positions of said first tube section with respect to said second tube section to form at least one sample port extending through both of said first and second tube sections.

27. A duct mountable detector, comprising:

a detector housing including a sensing cavity;

a first tube section connected to said detector housing open into said sensing cavity, said first tube extending to a distal end portion;

a second tube section having a first end portion connected to said first tube section, said second tube extending from said distal end portion of said first tube section, and having a second end opposite said first end portion, said second tube section having at least one sampling port open through said second tube section; and wherein said first tube section and said second tube section are connected together and are relatively adjustable for fixing the distance between said housing and said second end of said second tube section;

a plurality of holes spaced apart along a length of one of said first and second tube sections, and a fastener arranged to engage one of said holes of said plurality of said holes and a fixed position on a respective other of said first tube section and said second tube section;

wherein said plurality of holes is arranged on said second tube section, a portion of said second tube section telescopically nested inside said first tube section, and said first tube section includes at least one hole therethrough registrable with said plurality of holes at plural telescopic positions of said second tube section and said first tube section; and wherein said fastener comprises a screw fit into said hole of said first tube section and engaged into a select one of said plurality of said holes in said second tube section.

28. The detector according to claim 27, wherein said first tube section includes a plurality of spaced apart holes, said spaced apart holes are spaced apart along a length thereof at a same interval as said holes of said plurality of holes are spaced apart along said length of said second tube section and said screw extends into one pair of registering holes of said plurality of holes of said first and second tube sections to fix a relative position of said second tube section within said first tube section, and a plurality of pairs of holes of said first and second tube sections are in registry to function as air sampling ports.

29. A duct mountable detector, comprising:

a detector housing including a sensing cavity;

a first tube section connected to said detector housing open into said sensing cavity, said first tube extending to a distal end portion;

a second tube section having a first end portion connected to said first tube section, said second tube section extending from said distal end portion of said first tube section, and having a second end opposite said first end portion, said second tube section having at least one sampling port open through said second tube section; and wherein said first tube section and said second tube section are connected together and are relatively adjustable for fixing the distance between said housing and said second end of said second tube section;

a plurality of holes spaced apart along a length of one of said first and second tube sections, and a fastener arranged to engage one of said holes of said plurality of said holes and a fixed position on a respective other of said first tube section and said second tube section;

wherein said second tube section is sized to be partially nested into said first tube section, and comprising a plurality of first holes spaced apart along a length of said first tube section and a plurality of second holes spaced apart along a length of said second tube section with a same pitch as said first holes, said first tube section includes a reinforcing rib extending axially on an outside thereof, said plurality of first holes penetrating through said reinforcing rib; and comprising a fastener penetrating one of said first holes and one of said second holes to fix the relative axial position between said first and second tube sections.

* * * * *